(12) United States Patent
Huang et al.

(10) Patent No.: US 7,507,530 B2
(45) Date of Patent: Mar. 24, 2009

(54) NANOPARTICLE COMPLEXES HAVING A DEFINED NUMBER OF LIGANDS

(75) Inventors: Xueying Huang, Hockessin, DE (US); Zheng Ming, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 327 days.

(21) Appl. No.: 10/630,613

(22) Filed: Jul. 30, 2003

(65) Prior Publication Data

US 2005/0208142 A1      Sep. 22, 2005

Related U.S. Application Data

(60) Provisional application No. 60/406,211, filed on Aug. 27, 2002.

(51) Int. Cl.
*C12Q 1/68*      (2006.01)
*C12M 1/36*      (2006.01)
*G01N 15/06*     (2006.01)
*C07H 21/04*     (2006.01)

(52) U.S. Cl. .................. 435/6; 435/283.1; 435/287.2; 422/68.1; 422/82.01; 422/82.05; 536/23.1

(58) Field of Classification Search ................. None
See application file for complete search history.

(56) References Cited

U.S. PATENT DOCUMENTS 5,674,743 A * 10/1997 Ulmer ..................... 435/287.2

| | | | |
|---|---|---|---|
| 6,074,979 A | 6/2000 | Hagemeyer et al. | |
| 6,103,868 A | 8/2000 | Heath et al. | |
| 6,113,795 A | 9/2000 | Subramaniam et al. | |
| 6,261,779 B1 * | 7/2001 | Barbera-Guillem et al. | 435/6 |
| 6,361,944 B1 | 3/2002 | Mirkin et al. | |
| 6,958,216 B2 * | 10/2005 | Kelley et al. | 435/6 |

OTHER PUBLICATIONS

Alivisatos et al "Organizaiton of nanocrystal molecules using DNA" Nature, 1996, 382: 609-611.*
Mitchell, Gregory P. et al., Programmed Assembly of DNA Functionalilzed Quantum D ts, J. Am. Chem. Soc., 1999, 8122-8123, 121, American Chemical Society.
Mirkin, et al., A DNA-based methof for rationally assembling nanoparticles into macroscopic materials, Nature, vol. 382, p. 607, 1996.
Loweth et al., DNA-BasedAssembly of Gld Nanocrystals, Angew. Chem., Int. Ed. Engl. 1999, vol. 38, pp. 1808-1812.
Zanchet et al., Electrophoretic Isolation of Discrete Au Nanocrystal/sn/DNA Conjugates, Nano Lett. 2001, 1, pp. 32-35.
Niemeyer et al., Nucleic Acid Supercoiling as a Means for Ionic Switching of DNA—Nanoparticles Networks, Chembiochem, 2001, 2, pp. 260-264.
Wei et al., Separation of nanometer gold particles by size exclusion chromatography, J. Chromatogr. A 836, 253-260, 1999.

(Continued)

*Primary Examiner*—B J Forman

(57) ABSTRACT

A rapid method for the separation of nanoparticles having as few as one ligand attached thereto has been developed. The method relies on the size exclusion separation of a population of nanoparticle-ligand complexes having a narrow uniform size distribution. Ligands are typically biopolymers, functionalized to bind to other nanoparticles for the construction of geometric nanostructures.

7 Claims, 7 Drawing Sheets

Generation of Geometric Nano-structures

OTHER PUBLICATIONS

Wei et al., Shape Separation of anometer Gold Particles by Size-Exclusion Chromatography, Anal. Chem. 71: pp. 2085-2091, 1999.

Templeton et al., Water-Soluble, Isolable Gold Clusters Protected by Tiopronin and Coenzyme A Monolayers, Langmuir 15, pp. 66-76, 1999.

Chen et al., Poly(N-vinylisobutyramide)-stabilized platinum nanoparticles: syntheis and temperature-responsive behavior in aqueous solution, Colloids and Surfaces A 169: pp. 107-116, 2000.

Wuelfing et al., Nanometer Gold Clusters Protected by Surface-Bound Monolayers of Thiolated Poly(ethylene glycol)Polymer Electrolyte, J. Am. Chem. Soc. 120: 12696-12697, 1998.

Chan et al., Quantum Dot Bioconjugates for Ultrasensitive Nonisotopic Detection, Science 281, 2016-2018, 1998.

Mitchell et al., Programmed Assembly of DNA Functionalized Quantum Dots, J. Am. Che. Soc. 121: 8122-8123, 1999.

Napper, Steric Stabilization, J. Colloid. Interface. Sci. 58: pp. 390-407, 1977.

Schaaff et al., Isolation and Selected Properties of a 10.4 kDa Gold: Glutathione Cluster Compound, J. Phys. Chem., 102, pp. 10643-10646, 1998.

Whetten et al.,Nanocrystal Gold Molecules, Nanocrystal Gold Molecules, Adv. Mater. 8: 428-433, 1996.

* cited by examiner

Figures 1 (a)-(d)
Generation of Geometric Nano-structures

Gel electrophoresis of gold nanoparticles labeled with varying numbers of ssDNA strands Gel filtration of to gold nanoparticles labeled with 2, 1 and 0 ssDNA Gel electrophoresis of labelled gold nanoparticles Gold nanoparticle labeled with ssDNA

—SC$_6$H$_{12}$AAA AAA GCG TGG GCG TGG GCG TGG GCG TGG GCG [SEQ ID NO:1]

Gold nanoparticle labeled with complementary ssDNA

—SC$_6$H$_{12}$AAA AAA CGC CCA CGC CCA CGC CCA CGC CCA CGC [SEQ ID NO:2]

Dimer from prepared from Fig. 4a and 4b

Gel fitration of gold nanoparticles labeled with ssDNA

Gel electrophoresis of gold nanoparticles labelled with ssDNA

Figure 6B is an enlarged view of Figure 6A.

TEM of the dimers from Figures 5a and b

Gel fitration of gold nanoparticles labeled with ssDNA

Gel electrophoresis of gold nanoparticles labelled with ssDNA

SEQUENCE LISTING

<160> NUMBER OF SEQ ID NOS: 3

<210> SEQ ID NO 1
<211> LENGTH: 33
<212> TYPE: DNA
<213> ORGANISM: Artificial Sequence
<220> FEATURE:
<223> OTHER INFORMATION: 986-ZF
<220> FEATURE:
<221> NAME/KEY: misc_feature
<223> OTHER INFORMATION: C6-SH on 5' end

<400> SEQUENCE: 1
aaaaaagcgt gggcgtgggc gtgggcgtgg gcg        33

<210> SEQ ID NO 2
<211> LENGTH: 33
<212> TYPE: DNA
<213> ORGANISM: Artificial Sequence
<220> FEATURE:
<223> OTHER INFORMATION: 987-ZR
<220> FEATURE:
<221> NAME/KEY: misc_feature
<223> OTHER INFORMATION: C6-SH on 5' end

<400> SEQUENCE: 2
aaaaaacgcc cacgcccacg cccacgccca cgc        33

<210> SEQ ID NO 3
<211> LENGTH: 33
<212> TYPE: DNA
<213> ORGANISM: Artificial Sequence
<220> FEATURE:
<223> OTHER INFORMATION: 995-BR
<220> FEATURE:
<221> NAME/KEY: misc_feature
<223> OTHER INFORMATION: SH on 5' end, biotinylated on 3' end

<400> SEQUENCE: 3
aaaaaacgcc cacgcccgga tccacgccca cgc        33

NANOPARTICLE COMPLEXES HAVING A DEFINED NUMBER OF LIGANDS

This application claims the benefit of U.S. Provisional Application 60/406,211 filed Aug. 27, 2002, the disclosure of which is incorporated herein in its entirety by reference.

FIELD OF INVENTION

The invention relates to the preparation of metal nanoparticles having a defined number of ligands affixed thereto.

BACKGROUND

Nanoparticles are nanometer-sized metallic and semiconducting particles that are the subject of extensive research in the field of nanoscale materials. Nanoparticles have potential applications in many diverse fields, including nanoscale electronic devices, multifunctional catalysts, chemical sensors, and many biological applications such as biosensors, and biological assays. Self-assembled spatial positioning of nanoparticles is a requirement for the commercial development of many of these applications.

The preparation of nanoparticles covalently bound to one or more ligands has been demonstrated by many groups with a wide variety of ligands. In order to serve as construction elements or as diagnostic devices, the precise number of ligands per nanoparticle must be known. Due to statistical nature of chemical reactions, it is very difficult to obtain particles with a defined number of ligands via direct chemical transformation. Therefore, the need exists for separation methods to isolate nanoparticles on the basis of the number of ligands affixed to the nanoparticle.

Methods of separating nanoparticle—ligand complexes are known. For example, Mirkin, et al. (*Nature, Vol.* 382, pg. 607, 1996) teaches the use of oligonucleotides for the synthesis of gold nanoparticles into aggregate, macroscopic clusters. Loweth, et al. (*Angew. Chem., Int. Ed. Engl.* 1999, Vol 38, 1808-1812) prepared dimers of phosphine stabilized gold nanoparticles using complementary strands of ssDNA bound to each particle using gel electrophoresis to isolate the dimers from the reaction mixture. Zanchet, et al. (*Nano Lett.* 2001, 1, 32-35) demonstrate the electrophorectic separation of gold nanoparticles on the basis of the number of bound ssDNA strands, however the authors were unable to separate particles with ligands of lengths of less than 50 bases. Niemeyer et al. (*Chembiochem,* 2001, 2, 260-264) prepared nanoscale networks and aggregates using biotinylated DNA and strepavidin, but did not isolate individual structures.

The above described methods for the separation and isolation of nanoparticle—ligand complexes are useful, however suffer the disadvantage of not being able to reproducibly isolate nanoparticles comprising a single species of ligand in a rapid and facile manner.

Size exclusion chromatography (SEC), also known as gel permeation chromatography, is a liquid chromatographic technique that uses a permeable support to separation analytes by size. The advantage of this separation technique is that it is rapid, easily performed, and readily lends itself to large-scale operations.

SEC has been used to characterize and separate gold nanoparticles. For example, Wei et al. (*J. Chromatogr. A* 836, 253-260 (1999)) described the separation of gold nanoparticles between 5 and 38 nm in size using SEC with a polymer-based column of 100 nm pore size. The shape separation of gold nanoparticles using SEC has also been described (Wei et al., *Anal Chem.* 71:2085-2091 (1999)).

Although the technique of SEC has a long history, to date there is no report of its use for the purpose of separating nanoparticles with a narrow size distribution having a single ligand species affixed thereto. Applicants have solved the stated problem by developing an SEC technique that permits the separation and isolation of nanopaticle-ligand complexes having a distinct ligand species.

SUMMARY OF THE INVENTION

The invention provides a process for the generation of a nanoparticle comprising a defined number of ligands, the process comprising the steps of:

a) providing a population of nanoparticles having a narrow uniform size distribution, wherein a subset of the population has at least one ligand stably affixed to the nanoparticle to form a nanoparticle-ligand complex, wherein the minimum effective size of said complex is at least twice the effective size of the isolated nanoparticle;

b) applying the population of nanoparticles of (a) to a size exclusion chromatographic medium having an effective size cutoff greater than the nanoparticle-ligand complex; and c) collecting nanoparticle-ligand complexes having a defined number of ligands.

In another embodiment the invention provides a geometric nanostructure comprising at least three nanoparticle-ligand complexes, said complexes each comprising:

a) a nanoparticle;

b) a ligand having a first proximal portion and a second distil portion;

wherein the ligand is affixed to the surface of the nanoparticle at the first proximal portion; and wherein the nanoparticle-ligand complexes are each affixed to each other through the second distil portion of the ligand.

In a preferred embodiment the invention provides a geometric nanostructure comprising at least two nanoparticle-ligand complexes, said complexes each comprising:

a) at least one nanoparticle; and b) at least one ligand having a first proximal portion and a second distil portion;

wherein the ligand is affixed to the surface of the nanoparticle at the first proximal portion; and wherein the nanoparticle-ligand complexes are each affixed to each other through the second distil portion of the ligand, and take the forms of dimers, trimers, tetramers and mixtures thereof.

BRIEF DESCRIPTION OF THE FIGURES AND THE SEQUENCE LISTING

FIGS. 1(*a*)-(*d*) depict the generation of geometric nanostructures.

FIG. 2 is a gel electrophoresis of gold nanoparticles labeled with varying numbers of ssDNA strands FIGS. 3*a-b* depict the results from gel filtration and subsequent gel electrophoresis of gold nanoparticles labeled with ssDNA.

FIGS. 4*a* and *b* depict gold nanoparticles labeled with ssDNA and complementary ssDNA.

FIG. 4*c* depicts the dimer form prepared from FIGS. 4*a* and 4*b*.

FIGS. 5*a* and *b* depict the gel filtration and gel electrophoresis of gold nanoparticles dimers labeled with ssDNA.

Figure 7A:
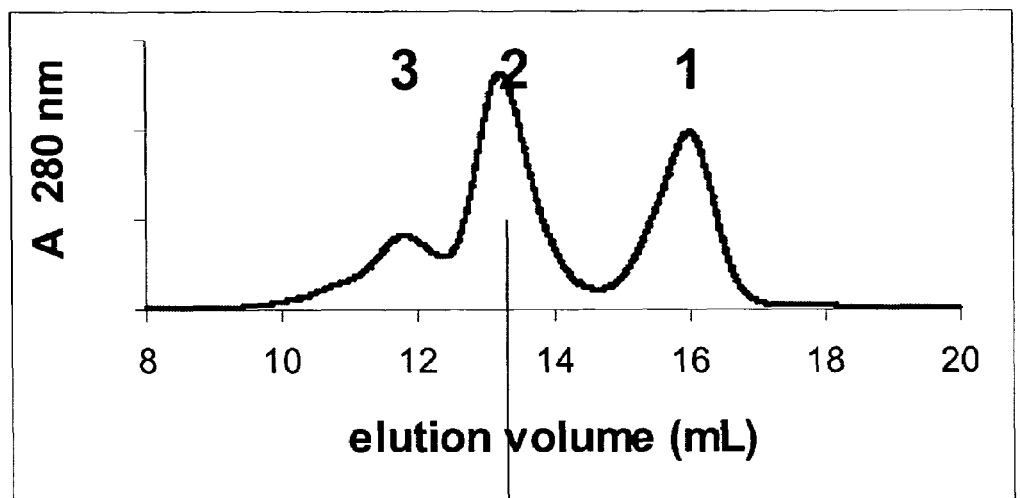
Figure 7B:
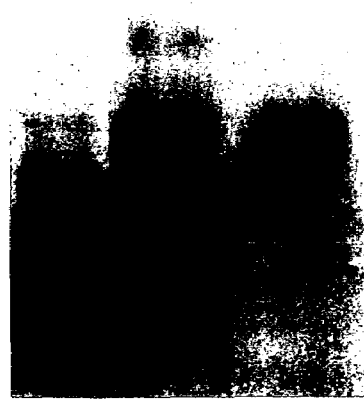

FIGS. 7a and b depict the gel filtration and gel electrophoresis of gold nanoparticles dimers labeled with biotinylated ssDNA.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requfirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-3 are nucleic acid ligands suitable for attachment to nanoparticles of the invention.

DETAILED DESCRIPTION OF THE INVENTION

The invention relates to a method for obtaining a nanoparticle or nanaoparticles with a defined number of ligands attached thereto. The ability to stoichometrically control the number of ligands on a nanoparticle enables quantitative control of the steps needed for synthesis of a variety of nanometer-scale electronic devices including electrically conductive geometric nanostructures field emission displays, and conductive coatings.

The following definitions and abbreviations will be used herein for the interpretation of the claims and the specification:

"CNBP" means Carbon nanotube binding peptide
"MWNT" means Multi-walled nanotube
"SWNT" means Single walled nanotube
"TEM" means transmission electron microscopy
"CNT" means carbon nanotube
"GSH" refers to the chemical compound glutathione.
"TP" is the abbreviation for tiopronin "Nanoparticles" are herein defined as metallic particles with an average particle diameter of between 1 and 100 nm. Preferably, the average particle diameter of the particles is between about 1 and 40 nm. As used herein, "particle size" and "particle diameter" have the same meaning.

The term "nanostructure" means tubes, rods, cylinders, bundles, wafers, disks, sheets, plates, planes, cones, slivers, granules, ellipsoids, wedges, polymeric fibers, natural fibers, and other such objects which have at least one characteristic dimension less than about 100 microns.

The terms "nanorod" means a variety of nano-structures which may be either hollow or solid and may or may not have a circular corssectional shape. Nano-rods of the invention may include nanotubes, nanofibers, polymeric nanofibers, bundles and multiwalled structures.

The term "nanotube" refers to a hollow article having a narrow dimension (diameter) of about 1-200 nm and a long dimension (length), where the ratio of the long dimension to the narrow dimension, i.e., the aspect ratio, is at least 5. In general, the aspect ratio is between 10 and 2000.

By "nanoplanes" is meant surfaces which have one characterstic dimension less than 500 nanometer, for example a single or a dual layer of graphite or graphene sheets.

By "nanofibers" is meant natural or polymeric filaments which have a small dimension of less than 1000 nanometer.

As used herein the term "narrow uniform size distribution" when used in reference to a population of nanoparticles means a population of nanoparticle where the size of any single nanoparticle varies by no more than about 10% from the mean size of the population.

A "monolayer" refers to a layer of material coated on a nanoparticle that is the thickness of single molecule.

A "mixed monolayer" refers to a monolayer having at least two different molecular components.

A "capture coating component" as used herein refers to a material capable of forming a monolayer on a nanoparticle that has an affinity for some ligand or capture moiety. The "capture" component makes up the lesser portion of a mixed monolayer and may comprise less than 50% of the monolayer.

A "shielding coating component" refers to a material capable of forming a monolayer on a nanoparticle that has the ability to prevent non-specific binding of substances that are not capture moieties. Shielding coating components may be comprised of a variety of materials where ethylene glycol is particularly suitable.

The term "nanoparticle-ligand complex" refers to a nanoparticle having at least one ligand stably affixed thereto.

The term "stably affixed" when used in reference to the attachment of a ligand to a nanoparticle or other nanostructure refers to the attachment of the ligand to the surface of the nanoparticle through covalent bonding or other chemical means.

The term "geometric nanostructure" refers to nanometer-scale structure comprising at least two nanoparticle-ligand complexes where the nanoparticles are spatially arranged in an ordered geometric pattern.

The term "ligand" means any material that may be bound to the surface of a nanoparticle or nanostructure for the linking of nanoparticles to form nanometer-scale geometric structures. Ligands are stably affixed to nanoparticles and other nanostructures at their "proximal portions" whereas the "distil portion" of the ligand is free to bind to another moiety.

The term "binding pair" refers to chemical or biopolymer based couples that bind specifically to each other. Common examples of binding pairs are immune-type binding pairs, such as antigen/antibody or hapten/anti-hapten systems.

The term "effective size" means the size of a material that appears in a size exclusion chromatography. The "effective size" of a material is distinguished from the "actual size" of a material in that materials may appear larger or smaller than they really are depending on their chemical and physical properties and their interaction with the size exclusion chromatographic media. The effective size of a material is determined as compared with materials of known sizes in size exclusion chromatography under the same conditions.

The term "size exclusion chromatographic medium" refers to any material that may be configured to produce a uniform pore size and used to separate nanometer-scale materials on the basis size.

As used herein a "nucleic acid molecule" is defined as a polymer of RNA or DNA that is single- or double-stranded, optionally containing synthetic, non-natural or altered nucleotide bases. An nucleic acid molecule in the form of a polymer of DNA may be comprised of one or more segments of cDNA, genomic DNA or synthetic DNA.

The term "peptide" refers to two or more amino acids joined to each other by peptide bonds or modified peptide bonds. Peptides include those modified either by natural processes, such as processing and other post-translational modifications, but also chemical modification techniques. The modifications can occur anywhere in a peptide, including the peptide backbone, the amino acid side chain, and the amino or carboxyl terminal. Examples of modifications include but are not limited to amidation, acylation, acetylation, cross linking, cyclization, glycosylation, hydroxylation, phosphorylation, racemization, and covalent attachment of various moieties such as nucleotide or nucleotide derivative, lipid or lipid derivatives (see, for instance, Proteins—Structure and Molecular Properties, 2nd Ed Creighton, W. H. Freeman and Company, New York (1993) and Post-translation covalent Modification of Proteins, B. C. Johnson, Ed., Academic Press, New York (1983)).

As used herein, the term "peptide" and "polypeptide" will be used interchangeably.

The term "peptide nucleic acids" refers to a material having stretches of nucleic acid polymers linked together by peptide linkers.

The invention relates to a method for the rapid and large-scale separation of a population of nanoparticle-ligand complexes of uniform size into fractions where the precise number of ligands per nanoparticle may be known. The nanopartilces may be optionally coated with a monolayer to stabilze the particle and to provide for water solubility. Once separated the nanoparticle may be assembled into nanometer-scale geometric structures that will useful in the construction of electronic nanodevices.

Nanoparticle—Ligand Complex

Nanostructures and Nanoparticles

The invention provides a complex formed by the linking of a ligand and a nanoparticle or nanostructure. Although nanoparticles have been exemplified herein, it will be appreciated by one of skill in the art that a variety of other nanostructures may be suitable. For example nanostructures suitable in the present invention may have a variety or shapes including tubes, rods, cylinders, bundles, wafers, disks, sheets, plates, planes, cones, slivers, granules, ellipsoids, wedges, polymeric fibers, natural fibers, and are limited only in that they should have at least one characteristic dimension less than about 100 microns.

For example, nanoplanes could be functionalized to receive a ligand and would take the shape of dumbells, rectangles, circles, ovals, or polygons, for example. Typical nanoplanes may be comprised of a variety of materials such as carbon graphene, metal oxides, silicates, metal sulfides, and other materials obtained by exfoliating layered minerals.

In one embodiment it is envisioned that nano-rods would be amenable to use in the invention. Nano-rods would include, but not be limited to nanotubes, and nanofibers, including carbon nanotubes, and polymeric nanofibers, bundles and multiwalled structures.

Particularly suitable nano-rods in the present invention are nanotubes, where carbon based nanotubes are most preferred. Nanotubes of the invention are generally about 1-200 nm in length where the ratio of the length dimension to the narrow dimension, i.e., the aspect ratio, is at least 5. In general, the aspect ratio is between 10 and 2000. Carbon nanotubes are comprised partially of carbon atoms, however may be doped with other elements, e.g., metals. The carbon-based nanotubes of the invention can be either multi-walled nanotubes (MWNTs) or single-walled nanotubes (SWNTs). A MWNT, for example, includes several concentric nanotubes each having a different diameter. Thus, the smallest diameter tube is encapsulated by a larger diameter tube, which in turn, is encapsulated by another larger diameter nanotube. A SWNT, on the other hand, includes only one nanotube.

Preferred in the invention for the formation of a nanostructure-ligand complex is a nanoparticle. Suitable nanoparticles are metallic or semiconductor particles with an average particle diameter of between 1 and 100 nm. Preferably, the average particle diameter of the particles is between about 1 and 40 nm. The metallic nanoparticles include, but are not limited to, particles of gold, silver, platinum, palladium, iridium, rhodium, osmium, iron, copper, cobalt, and alloys composed of these metals. The "semiconductor nanoparticles" include, but are not limited to, particles of cadmium selenide, cadmium sulfide, silver sulfide, cadmium sulfide, zinc sulfide, zinc selenide, lead sulfide, gallium arsenide, silicon, tin oxide, iron oxide, and indium phosphide.

The nanoparticles of the invention are coated with a monolayer. The monolayer serves as an attachment for a suitable ligand, and also serves to render the nanoparticle water soluble. Nanoparticles that have been rendered water soluble by coating are referred to herein as "stabilized". Methods for the preparation of stabilized, water-soluble metal and semiconductor nanoparticles are known in the art. These particles can be either charged or neutral depending on the nature of the organic coating. For example, Templeton et al. (*Langmuir* 15:66-76 (1999)), herein incorporated by reference, describe a method for the preparation of stabilized, charged, water-soluble gold nanoparticles protected by tiopronin or coenzyme A monolayers. To prepare the tiopronin-protected gold nanoparticles, tetrachloroauric acid and N-(2-mercaptopropionyl)glycine (tiopronin) were codissolved in a mixture of methanol and acetic acid. Sodium borohydride was added with rapid stirring. The average particle size of these particles could be controlled by varying the mole ratio of tiopronin to tetrachloroauric acid in the reaction. The coenzyme A protected gold nanoparticles were prepared in a similar manner by substituting coenzyme A for tiopronin in the reaction.

A similar method of preparing stabilized, water-soluble nanoparticles of the metals gold, silver, platinum, palladium, cobalt and nickel is descried by Heath et al. in U.S. Pat. No. 6,103,868, herein incorporated by reference. In this method, a solution or dispersion of one or more metal salts was mixed with a solution of an organic surface passivant that had a functional group such as a thiol, phosphine, disulfide, amine, oxide, or amide. A reducing agent was then added to reduce the metal salt to the free metal.

A method for preparing stabilized, water soluble platinum nanoparticles is described by Chen et al. (*Colloids and Surfaces A* 169:107-116 (2000)), herein incorporated by reference. These nanoparticles were prepared in an ethanol-water mixture by the reduction of chloroplatinic acid by ethanol in the presence of poly(N-vinylisobutyramide).

Hagemeyer et al. in U.S. Pat. No. 6,074,979, herein incorporated by reference, described a method for preparing polybetaine-stabilized palladium nanoparticles by reacting a palladium salt, such as palladium acetate, with a reducing agent, such as sodium borohydride, in the presence of a polybetaine.

Stabilized, neutral, water-soluble metal nanoparticles are prepared using the methods described above using a nonionic stabilizing organic coating or monolayer. For example, Wuelfing et al. (*J. Am. Chem. Soc.* 120:12696-12697 (1998)), herein incorporated by reference, described the preparation of neutral, water-soluble gold nanoparticles protected by a monolayer of thiolated poly(ethylene glycol).

Stabilized, charged, water soluble semiconductor nanoparticles can also be produced by various known methods. For example, Chan et al. (*Science* 281:2016-2018 (1998)), herein incorporated by reference, described a method for preparing zinc sulfide-capped cadmium arsenide nanoparticles by reacting the nanoparticles with mercaptoacetic acid in chloroform. Another method for preparing stabilized, charged, water-soluble semiconductor nanoparticles is described by Mitchell et al. (*J. Am. Chem. Soc.* 121:8122-8123 (1999)), herein incorporated by reference. In this method, cadmium selenide/zinc sulfide nanoparticles were coated with a mixture of trioctylphosphine oxide and trioctylphosphine. These nanoparticles were then reacted with excess 3-mercaptopropionic acid in dimethyl formamide to form propionic acid-functionalized nanoparticles.

Stabilized, neutral, water-soluble semiconductor nanoparticles can be prepared by coating the particles with a nonionic organic stabilizing compound, such as poly(ethylene oxide) or poly(vinyl alcohol), as described by Napper (*J. Colloid. Interface. Sci* 58:390-407 (1977)).

For both stabilized, water-soluble semiconductor and metal nanoparticles it is possible to use mixtures of various stabilizing coatings or monolayers, for example, poly(ethylene glycol) and glutathione or poly(ethylene glycol) and tiopronin.

Alternatively it may be useful to provide a nanoparticle coated with a mixed monolayer where one component of the monolayer provides a point of attachment for the ligand, and the other component of the mixed monolayer acts as a shield against non-specific binding of undesired proteins or capture moieties. In this embodiment, typically the mixed monolayer having a capture component and a shielding component are part of the same monolayer. Typically the capture component comprises less than about 50% of the mixed monolayer where about 20%-40% is preferred. Conversely the shielding component forms the major component of the monolayer and comprises at least about 50% of the monolayer, where 60% to about 90% is preferred.

The capture component of any such mixed monolayer must have the ability to bind the bifuctional peptides of the invention. The capture component may be functionalized with various chemical groups that allow for binding to a ligand. Non-limiting examples of such chemical reactive groups include those selected from the group consisting of: —$NH_2$, —COOH, —CHO—, —OH, —X (Cl, Br, I), succinimide, and epoxy groups. Preferred examples of suitable capture components are tiopronin and GSH. Tiopronin (abbreviated TP), is N-2-mercaptopropionyl-glycine is particularly suitable as a capture component because of the presence of exposed carboxy groups which serve as a convenient binding site for biopolymer lignads such as nucleic acids and peptides.

The shielding component of the mixed monolayer serves to block the binding of non-lignad materials to the coated nanoparticle and permits the nanoparticle to be used to bind, isolate or immobilize specific biopolymer ligands and the like. Suitable shielding components will include but are not limited to short chain ethylene glycol oligomers, ethylene glycol methacrylate, sugars, crown ethers, and acrylamide, where the short chain ethylene glycol oligomers are preferred.

Ligands

The nanoparticle-ligand complex will comprise a ligand that is affixed on the surface of the nanoparticle for the linking of a number of complexes in geometric conformations.

Ligands suitable in the invention will include without limitation of proteins, nucleic acids, peptide nucleic acids, synthetic polymers and oligomers. Preferred in the present invention are nucleic acid containing ligands such as DNA, RNA and peptide nucleic acids. Nucleic acid ligands may be single stranded or double stranded and will generally range from about 10 bases to about 100 bases where a length of about 20 bases to about 50 bases is preferred.

The ligands of the invention may be derivitized to comprise functional groups at their distil ends. These functional groups may be useful in allowing the ligand to bind to other coated nanoparticles, or alternatively other capture moieties such as proteins. So for example the functional group could be a member of a binding pair such as for example, Glutathione-S-transferase/glutathione, 6× Histidine Tag/Ni-NTA, Streptavidin/biotin, S-protein/S-peptide, Cutinase/phosphonate inhibitor, antigen/antibody, hapten/anti-hapten, folic acid/folate binding protein, and protein A or G/immunoglobulins.

In the case of nucleic acid ligands either the 5' or 3' end of the nucleic acid molecule may be derivatized with a variety of functional groups and spacers to effect binding. For example, a non-limiting list of functional groups include $SC_6H_{12}$, amine groups (—NH2) with 1 to 12 carbon spacers, thiol groups (SH) with 1 to 12 carbon spacers, biotin groups with 1 to 12 carbon spacers or triethylene glycol spacers, and acrylamide groups with 1 to 12 carbon spacers.

Synthesis of Ligand-Nanoparticle Complexes

Ligands may be stably affixed to the surface of a prepared nanostructure such as nanoparticle coated with a momolayer by a variety of methods well known in the art. Where the ligand is a peptide for example, the peptide can be affixed to the coated nanoparticles by a variety of methods, falling generally into two categories according to the chemical nature of linkage: covalent and non-covalent. The covalent linking method employs a small cross-linker molecule to react with a functional group on the coated nanoparticles and one on the ligand. The basic principle of and many cross-linker molecules for the method are well-described in the literature (*Bioconjugate Techniques* by Greg T. Hermanson. Academic Press, San Diego, Calif., 1996). One example of this method uses molecule EDC [1-ethyl-3-(3-dimethylaminopropyl)carbodiimide hydrochloride] to cross-link a carboxylic group on the coated nanoparticle (Au-Tp, for instance)) and a amine group on the ligand.

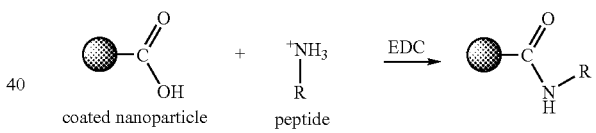

The noncovalent method employs nocovalent interaction between a ligand pre-affixed on the coated nanoparticle (Au-GSH, for example) and the corresponding ligand-binding domain (GST for Au-GSH) of the ligand. A variety of ligand/ligand binding domain pairs can be used for the purpose, as described in previous text.

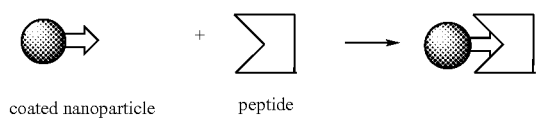

Where the ligand is a nucleic acid molecule, it may be modified at the 5' or 3' end with a variety of functional groups that will allow for binding to the monolayer or to the nanoparticle surface directly. The type of functional group will of course depend on the nature of the monolayer and the nanoparticle itself. Where for example, the monolayer is comprised of a matrix such as tiopronin or other —SH containing molecules, the chemical functional group may be attached to the 5' or 3' end of the ligand. The modified ligand may be affixed to nanoparticles through ligand replacement reaction.

Isolation of Ligand-Nanoparticle Complexes Having a Defined Number of Ligands The method of the invention provides for the isolation of a population of nanoparticle-ligand complexes having a defined number of ligands affixed to the nanoparticle. In a preferred embodiment this is accomplished by subjecting a population of nanoparticles-ligand complexes having a narrow uniform size distribution to size exclusion chromatography. The size of any nanoparticle within the starting population should not vary from the mean size of the population by any more than about 20% where no more than 10% is preferred. Populations having a narrow uniform size distribution may be prepared by a variety of methods including gel electrophoresis (see Schaaff et al. (*J. Phys Chem.* 102:10643-10646), and two phase extraction methods (see for example Whetten et al. (*Adv. Mater.* 8:428-433 (1996); Subramaniam et al. in U.S. Pat. No. 6,113,795). Preferred in the present invention is a method that employs a biphasic separation scheme involving the combination of an aqueous solvent and water miscible organic solvent. Typically stabilized, charged, water-soluble nanoparticles having a broad size distribution are fractionated based upon the size of the nanoparticles by adding a substantially water-miscible organic solvent in the presence of an electrolyte. As used herein a "broad size distribution" in reference to a population of nanoparticles will refer to nanoparticles ranging in size from about 1 nm to about 100 nm, wherein the majority of nanoparticles are spread over a large range of particle sizes.

A substantially water-miscible organic solvent is herein defined as an organic solvent that dissolves completely in water up to a concentration of at least 80% by volume. Suitable organic solvents include, but are not limited to, methanol, ethanol, isopropanol, dimethyl sulfoxide, tetrahydrofuran, dimethylformamide, dioxane, and acetone. Suitable organic solvents also include mixtures of organic solvents that are completely miscible with each other and that result in a mixture which is a substantially water-miscible organic solvent. Examples of mixed solvents include, but are not limited to, ethyl acetate and methanol; ethyl acetate and ethanol; ethyl acetate and isopropanol; ethyl acetate and acetone; ethyl acetate, dimethylformamide and dimethyl sulfoxide; and ethyl acetate, tetrahydrofuran, and dioxane. The preferred organic solvent is methanol or ethanol. The electrolytes that can be used include, but are not limited to, sodium chloride, sodium phosphate, sodium citrate, sodium acetate, magnesium sulfate, calcium chloride, ammonium chloride, and ammonium sulfate. The divalent metal ion salts appear to work better with nanoparticles that are stabilized with mixed coatings, such as poly(ethylene glycol) and glutathione, than with nanoparticles that are stabilized with single component coatings. The preferred electrolyte is sodium chloride.

In order to fractionate the stabilized, charged, water-soluble nanoparticles, the particles are first dissolved in an aqueous electrolyte solution having an electrolyte concentration of about 10 to 500 mM. Then, an addition of the substantially water-miscible organic solvent is made. The amount of the substantially water-miscible organic solvent added depends on the average particle size desired. The appropriate amount can be determined by routine experimentation. Typically, the substantially water-miscible organic solvent is added to give a concentration of about 5% to 10% by volume to precipitate out the largest particles. The nanoparticles are collected by centrifugation or filtration. Centrifugation is typically done using a centrifuge, such as a Sorvall® RT7 PLUS centrifuge available from Kendro Laboratory Products (Newtown, Conn.), for about 1 min at about 4,000 rpm. For filtration, a porous membrane with a pore size small enough to collect the nanoparticle size of interest can be used.

Optionally, sequential additions of the substantially water-miscible organic solvent are made to the nanoparticle solution to increase the solvent content of the solution and therefore, precipitate out nanoparticles of smaller sizes. The number of additions and the volume of the additions depend on the desired size distribution of the nanoparticles and can be determined by routine experimentation. Typically, additions of the substantially water-miscible organic solvent are made to increase the solvent content of the nanoparticle solution by about 5-15% by volume with each addition, up to a solvent concentration of about 70% by volume, which is sufficient to precipitate the smallest particles. The nanoparticles are collected after each addition as described above and the subsequent additions of the substantially water-miscible organic solvent are made to the supernatant. The collected nanoparticles are redissolved in water and the particle size distribution of the fractions can be determined using transmission electron microscopy (TEM), as described by Templeton et al. (*Langmuir* 15:66-76 (1999)). The average particle size of the fractions can be determined using the gel electrophoresis method described below.

In another embodiment of the present invention, stabilized, neutral, water-soluble nanoparticles are fractionated based upon the size of the nanoparticles by adding a substantially water-miscible organic solvent in the absence or presence of an electrolyte. The presence of an electrolyte is not required for fractionating stabilized, neutral, water-soluble nanoparticles, although the presence of an electrolyte is not detrimental. The method for fractionating stabilized, neutral, water-soluble nanoparticles is identical to the method described above for fractionating stabilized, charged, water-soluble nanoparticles except that the nanoparticles are initially dissolved in water without or with an electrolyte present. The preferred method is to dissolve the stabilized, neutral, water-soluble nanoparticles in water in the absence of an electrolyte.

Once a population of nanoparticles having a narrow uniform size distribution is obtained they may be complexed with a suitable ligand according to the methods described above. The population of nanoparticle-ligand complexes is then subjected to size exclusion chromatography (SEC) for fractionation. In this manner complexes having a defined number of ligands may be obtained. Any size exclusion separation medium may be used for this purpose where a carbohydrate based size exclusion medium is preferred. Size exclusion separation methods offer a rapid and large scale system for isolation of nanaoparticles having a defined number of ligands. Inherent in the process for separation is the fact that the effective size of the nanoparticle-ligand complex should be at least twice that of the nanoparticle lacking the ligand. Where the effective size of the complex is significantly below this the ability to isolate a complex having only one ligand attached is compromised. Additionally the choice of pore size for the SEC medium will depend on the size of the complex, however in any event should be greater than the effective size of the complex. For complexes in the range of about 2 nm to about 10 nm a SEC medium having a molecular weight cutoff of about 1000 kDA is suitable, where a cutoff of about 200 kDA is preferred. One preferred medium for use in the present invention is Superdex™ 200 gel filtration media.

Generation of Geometric Nano-structures

Once the nanoparticle-ligand complexes of the invention are isolated they may be used to generate geometric nanostrucutres that will form the basis of nanocircuits and the like.

Figure 1:
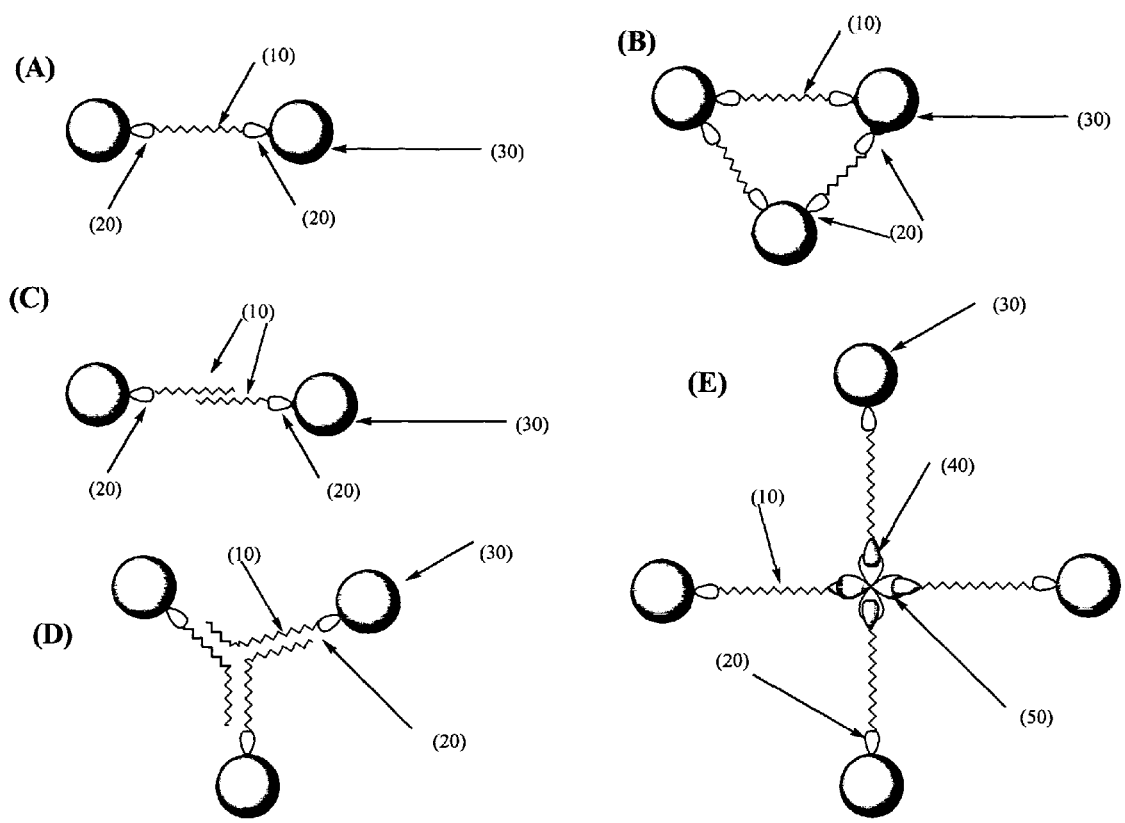

Nanoparticles may be linked together in a variety of conformations including dimers, trimers tetramers and combinations thereof. Examples of typical conformations are illustrated in FIG. 1 parts A-D.

In, FIG. 1(A) the simplest combination is shown. Here a ligand (10) may be functionalized on both the proximal and distil ends with a functional group (20) having affinity for the nanoparticle (30). Typically the ligand will be a nucleic acid or peptide and the functional groups will bind to a coating on the nanoparticle.

One of skill in the art will appreciate that this system is amenable to the construction of trimers as shown in FIG. 1(B).

Alternatively where the ligand is a single stranded nucleic acid or peptide nucleic acid the attachments between nanoparticles may be made at the distil portions of the ligands through hybridization as illustrated in FIG. 1(C). Alternatively hybridization of nucleic acid ligands may be use to create trimers as shown in FIG. 1(D) and other DNA architectures made by cross-hybridization of more than two single-stranded DNA.

In yet another embodiment it is contemplated that the complexes may be configured through the distil portions of the ligand by binding to a member of a binding pair that governs the geometry of the structure. An example of this scheme is shown in FIG. 1(E). Referring to FIG. 1(E) the ligand (10) may be functionalized at the proximal portion with a functional group (20) that has affinity for the nanoparticle (30). The distil portion of the ligand may then be functionalized with a first member of a binding pair such as biotin (40). The nanaoparticle-ligand complexes may then be brought into contact with the second member of the binding pair, streptavidin for example (50). Where the second member of a binding pair attains a specific geometric conformation it will convey this same conformation on the geometric nanostructure, here defining a tetrameteric heterojunction.

Where the nanoparticle is metallic or a semiconductor they may be assembled in the fashion described above to form heterojunctions and interconnects at the nano-scale. In the metallic case, the configured nanoparticles are expected to be able to link nanometer scale electronic devices together permitting the fabrication of high density electronic circuits. It is contemplated that it will be possible to array the metallic nanoparticles in an arrangement, where the distance between adjacent nanoparticle can be controlled by the potential difference between them, then the matrix could be used as a non-volatile memory device similar to that proposed by Leiber and collaborators (Rueckes T. et al. (2000). *Science* 289, 94-97) for carbon nanotubes.

Semiconducting nanoparticles could find use in 3-terminal gated devices which can be used directly as switches, amplifiers or logic gates. By linking the metal particles with organic semiconductors, it will be possible to develop 2-terminal switching devices, showing, for example, negative differential resistance (e.g. Fan et al. (2002) *JACS* 124, 5550-5560). Other possible applications include point sources for emission in field-emission display devices and as conductive inclusions in conductive coatings.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Unless otherwise specified, all the reagents were purchased from Aldrich Chemicals (Milwaukee, Wis.) and used without further purification.

The meaning of abbreviations is as follows: "h" means hour(s), "min" means minute(s), "sec" means second(s), "d" means day(s), "mL" means milliliters, "L" means liters.

Example 1

Particle Size Fractionation of Tiopronin Monolayer-Protected Gold Nanoparticles

The purpose of this Example was to prepare uniform size tiopronin monolayer-protected gold nanoparticles. The method comprises the fractional precipitation of the stabilized, charged, water-soluble nanoparticles by addition of a substantially water-miscible organic solvent in the presence of an electrolyte.

Preparation of Tiopronin Monolayer-Protected Gold Nanoparticles

Unless otherwise noted, all reagents were purchased from Aldrich (Milwaukee, Wis.) and were used without further purification. In a typical reaction, 60 mL of methanol (HPLC grade) and 10 mL of acetic acid (HPLC grade) were mixed in an Erlenmeyer flask by stirring for 2-5 min. Tetrachloroauric acid ($HAuCl_4 \cdot xH_2O$, 99.99%) (0.37 g) and 16.32 mg of N-(2-mercaptopropionyl)glycine (tiopronin) (99% minimum, obtained from Sigma, St. Louis, Mo.) were added to the above mixed solvents and dissolved by stirring for 5 min, resulting in a clear, yellow solution. A sodium borohydride solution was prepared by dissolving 0.6 g of $NaBH_4$ (99%) in 30 g of Nanopure® water. The $NaBH_4$ solution was added dropwise into the above solution with rapid stirring. When the first drop of $NaBH_4$ solution was added, the $HAuCl_4$ solution immediately turned dark brown from yellow. This reaction was exothermic, warming the solution for approximately 15 min. During the reaction, the pH of the solution changed from 1.2 to about 5.0. The reaction solution was stirred rapidly for 2 h. The tiopronin monolayer-protected gold nanoparticles were soluble in water and when diluted, the solution became clear purple.

Fractionation of Nanoparticles

The tiopronin monolayer-protected gold nanoparticles (0.3 g) were dissolved in 50 mL of a 100 mM sodium chloride solution. The first fraction of the nanoparticles was precipitated out by adding methanol to the nanoparticle solution to a final content of 10% by volume. The nanoparticles were collected by centrifugation at 4000 rpm for 1 min in a Sorvall® RT7 PLUS centrifuge (Kendro Laboratory Products, Newtown, Conn.). Then, more methanol was added to the supernatant to a final content of 20% by volume and the precipitated nanoparticles were collected as described above as the second fraction, which were used for the following experiments.

Example 2

Labeling Gold Nanoparticles with Single-Stranded DNA

In this and other examples, single-stranded DNA (ssDNA) oligo nucleotides were purchased from Integrated DNA Technologies, INC (Coralville, Iowa), with 5' C6 SH modification. The materials were used as received without further treatment. For this example, a ssDNA with sequence:

```
986-ZF:
                                          [SEQ ID NO:1]
    AAA AAA GCG TGG GCG TGG GCG TGG GCG TGG GCG
``` was used. Gold particles used in this and all other examples were Au-Tp particles prepared in EXAMPLE 1, with a concentration of 60 µM in H₂O. A titration experiment was set up by mixing appropriate amount of Au-Tp, ssDNA, NaCl, and H₂O, as shown in the following table, in order to determine optimal ratio of Au-Tp vs. ssDNA for labeling reaction.

|                | Rxn 1 | Rxn 2 | Rxn 3 | Rxn 4 | Rxn 5 | Rxn 6          |
|----------------|-------|-------|-------|-------|-------|----------------|
| Au-Tp (60 µM)  | 3     | 3     | 3     | 3     | 3     | 3              |
| SsDNA (40 µM)  | 0     | 1     | 2     | 4     | 8     | 1.6 (400 µM)   |
| NaCl (1M)      | 1.5   | 1.5   | 1.5   | 1.5   | 1.5   | 1.5            |
| H2O            | 10.5  | 9.5   | 8.5   | 6.5   | 2.5   | 8.9            |
| Total (µL)     | 15    | 15    | 15    | 15    | 15    | 15             |

Volume unit = µL

Figure 2:
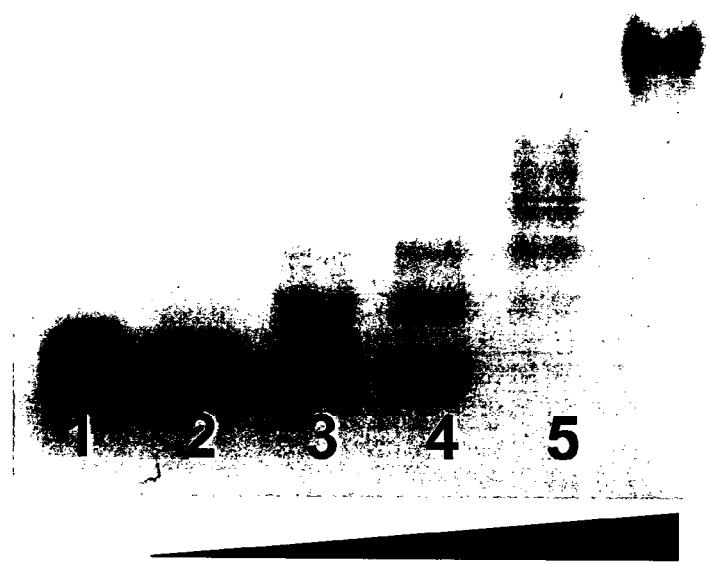

Each reaction was carried out in a 1.5 mL volume test tube. The reaction mixture was incubated at 60° C. for 15 min and allowed to slowly cool down to room temperature in 30 min. The products were analyzed by gel electrophoresis using a 4% agarose/Tris-Borate-EDTA (TBE) gel [BioWhittaker, Rockland, Me.). The gel was immersed in 1×TBE running buffer (89 mM Tris, 89 mM boric acid, 2 mM EDTA, pH=8.3), and electrophoresis was carried out at a constant voltage of 90 V for 80 min in a Horizon 58 gel box (Life Technologies, Rockville, Md.). The gel image (FIG. 2) was recorded using a HP ScanJet 6300C scanner (Agilent Technologies, Wilmington, Del.). Lanes 1 to 6 corresponds to reactions 1 to 6, respectively.

The result of this experiment shows that Au particles with different number of ssDNAs labeled can be clearly resolved by a 4% agarose gel; as the ratio of ssDNA vs. Au-Tp increases, more ssDNAs can be found on a particle. Thus, the stoichiometry of ssDNA and Au-Tp can be used to control the average number of ssDNA s on the surface of Au particles.

Example 3

Separation of Gold Nanoparticles with Different Number of Single-Stranded DNAs This example demonstrates that one can use size exclusion chromatography to obtain Au particles with exact number of ssDNAs attached. In this experiment, labeling reaction was done as follows. To 100 ul of Au-Tp (60 µM) was added 8 µL of 400 µM ssDNA (986-ZF) and 12 µL of 1 M NaCl. The reaction mixture was incubated at 60° C. for 15 min and allowed to slowly cool down to room temperature in 30 min.

Figure 3A:
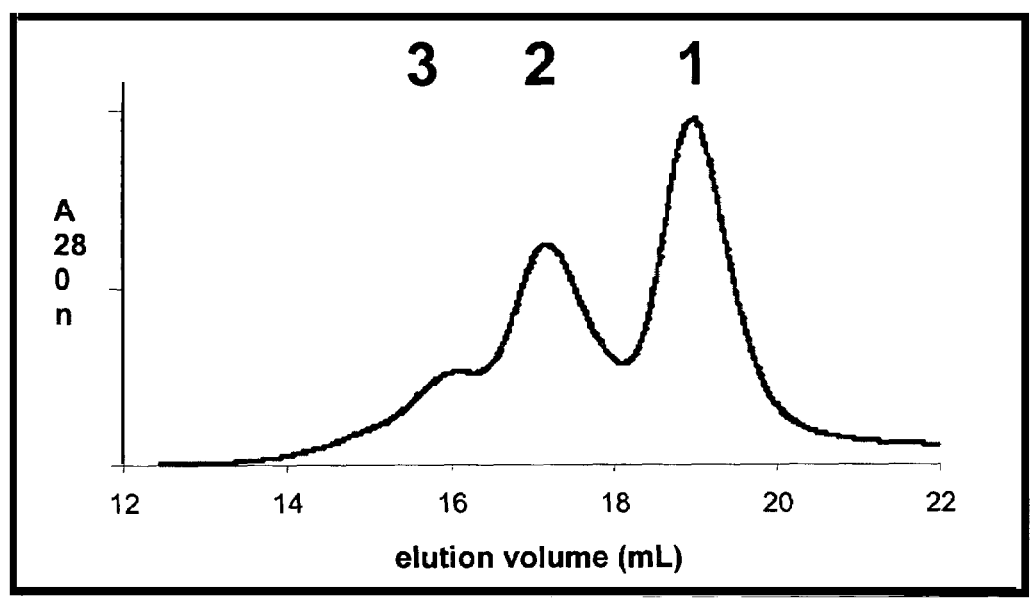
Figure 3B:
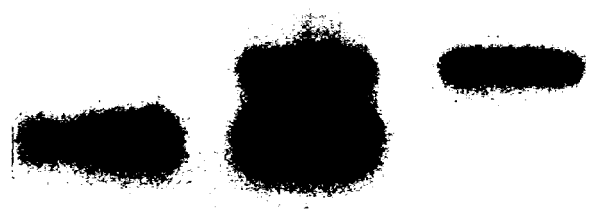

The above-mentioned reaction mixture was then injected into a Superdex 200 gel filtration column (Amersham Biosciences, Piscataway, N.J.) mounted on a BioCAD/SPRINT HPLC system (PerSeptive Biosystems, Framingham, Mass.), and eluted with 0.05 NaCl/0.15 M NaHPO4 buffer (pH 7) at a flow rate of 0.5 mL/min. The elution profile is shown in FIG. 3A. Peak 1,2 and 3 corresponds to nanoparticles labeled with 2, 1 and 0 ssDNA. In FIG. 3B, a gel image is shown comparing Au-Tp (lane1), Au-Tp/ssDNA reaction mix (lane 2), and the column fraction corresponding to peak 2 in FIG. 3A (lane 3). The gel mobility of the peak 2 fraction is consistent with the material being one-particle/one-ssDNA species. Further evidence supporting such an assignment is provided by the next example.

Example 4

Figure 4A:

Synthesis of Dimeric Gold Nanoparticle Structures Starting from One-Particle/One-ssDNA Species By following the procedure described in Example 3, gold particles were labeled with a ssDNA with sequence. The results are shown in FIGS. 4a and b. FIG. 4a depicts the gold nanoparticle from Example 2 labeled with sequence 986-ZF: AAA AAA GCG TGG GCG TGG GCG TGG GCG TGG GCG [SEQ ID NO: 1].

Figure 4B:

FIG. 4b depicts a gold nanoparticle prepared as above labeled with the complementary ssDNA sequence: 987-ZR: AAA AAA CGC CCA CGC CCA CGC CCA CGC CCA CGC.[SEQ ID NO: 2]

Figure 4C:

The 987-ZR was designed to have the last 27 nucleotides complementary to the last 27 nucleotides in 986-ZF, so that when 1 and 2 are mixed, a dimeric particle cluster should form due to DNA base pairing interactions, shown in FIG. 4c.

Figure 5A:
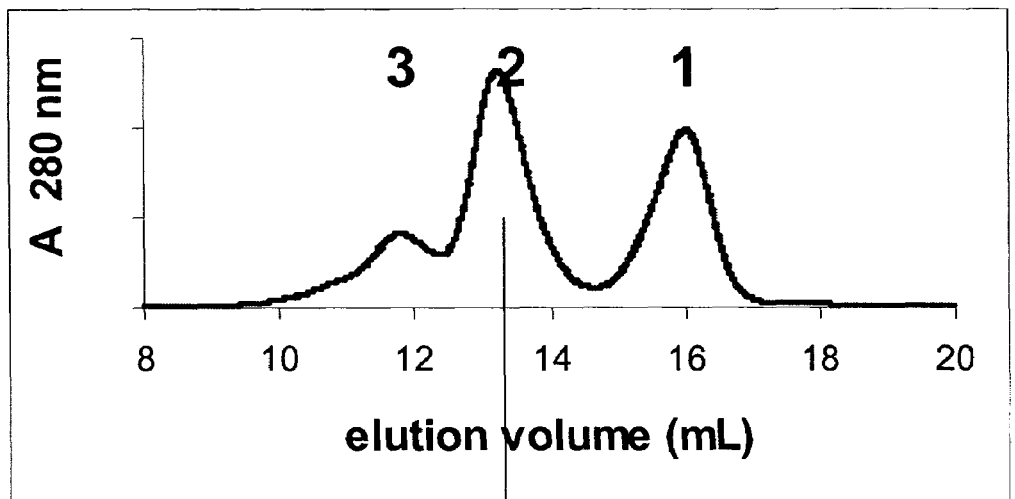
Figure 5B:
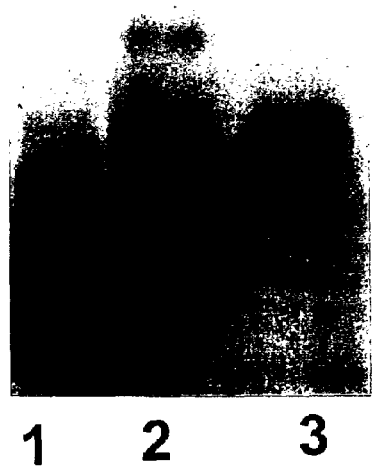

Both 4a and 4b were suspended in 0.05 NaCl/0.15 M NaHPO4 buffer (pH 7) at a concentration of 20 (M. Hybridization reaction was done by mixing 50 (L of 4a and 50 (L of 4b, followed by 15 min incubation at 60° C. The reaction mixture was then allowed to cool down to room temperature in 2 hrs. The hybridization mixture was injected into a Superdex 200 gel filtration column (Amersham Biosciences, Piscataway, N.J.) mounted on a BioCAD/SPRINT HPLC system (PerSeptive Biosystems, Framingham, Mass.), and eluted with 0.05 NaCl/0.15 M NaHPO4 buffer (pH 7) at a flow rate of 0.5 mL/min. The elution profile is shown in FIG. 5A. In addition to the major product eluted in peak 2, side-products represented by peak 1 and 3 were noticeable. These arise from the impurities in starting materials 4a and 4b, which contain small fraction of particles with 0, 2 and more number of ssDNA attached. (In preparation of 4a and 4b, there is a trade off between yield and purity.) In FIG. 5B, a gel image is shown comparing Au-Tp/ssDNA(986-ZR) reaction mix (lane 1), hybridization reaction mix of 4a and 4b (lane 2), and column fraction corresponding to peak 2 in FIG. 5A (lane 3). The gel mobility of the peak 2 fraction is consistent with its being a dimer species.

Figure 6B:
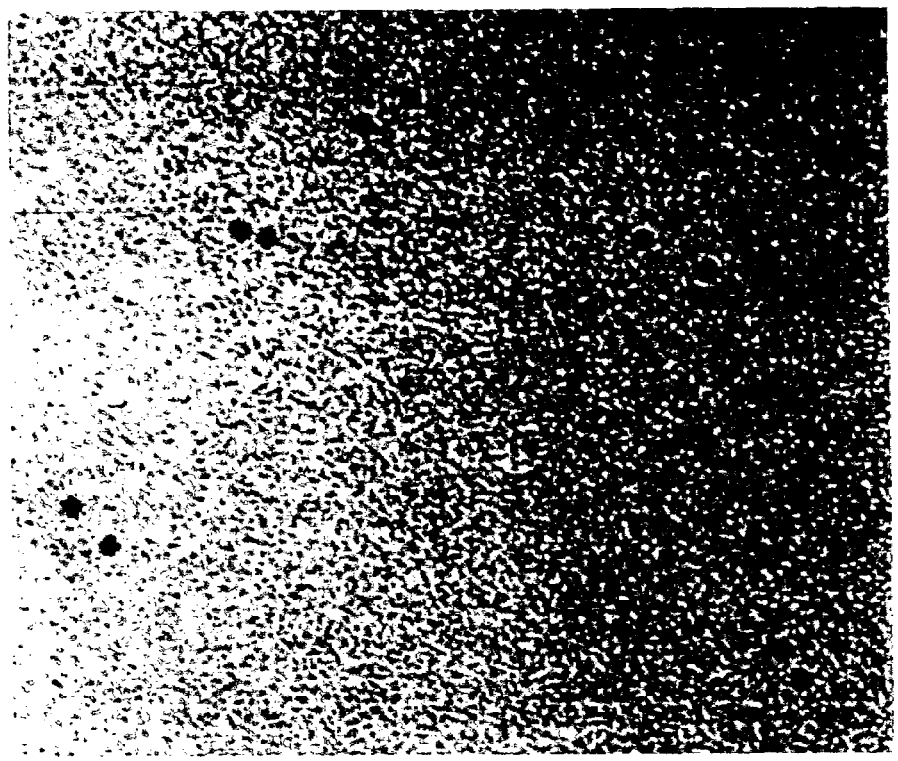
FIG. 6B is an enlarged view of some dimer structures from FIG. 6A.
Figure 6A:
FIG. 6A is a field view from TEM of the dimers from FIGS. 5*a* and 5*b*.

This material was also analyzed by transmission electron microscopy (TEM), which was done with an electron voltage of 200 kV and a 500K magnification using a JEOL-2011 transmission electron microscope. FIG. 6A is a larger field view from TEM. Quantitatively, more than 90% of purified

Example 5

Labeling Gold Nanoparticles with Single Biotin Molecule

This example illustrates the fixing of biotin to a nanoparticle for the attachment of a DNA ligand.

In this particular example, a ssDNA with 5'-SH and 3'-biotin (IDT) modification was used as follows:

995-BR:
[SEQ ID NO:3]
5'SH-AAA AAA CGC CCA CGC CCG GAT CCA CGC CCA CGC 3'-biotin.

A labeling reaction and gel filtration column separation were carried out as described in EXAMPLE 3 and 4, except that the ssDNA 995-BR was used. As shown in FIGS. 7A and B, the gel mobility of the peak 2 fraction is consistent with the material being one-particle/one-ssDNA/biotin species.

---

What is claimed is:

1. A geometric nanostructure comprising:
   at least three metallic nanoparticle-ligand complexes spatially arranged in an ordered geometric pattern, said complexes each comprising:
   a) one metallic nanoparticle; and
   b) one single stranded DNA ligand having
      i) a proximal portion affixed to the surface of the metallic nanoparticle; and
      ii) a distal portion;
   wherein said one single stranded DNA ligand is the only ligand unit affixed to the surface of said metallic nanoparticle, and
   wherein the nanoparticle-ligand complexes are each affixed to each other through the distal portion of each respective ligand.

2. A geometric nanostructure according to claim 1 wherein the nanoparticle has a diameter of about 2 nm to about 10 nm.

3. A geometric nanostructure of claim 1 wherein the ligand is derivatized to include a functional group at the distal portion.

4. A geometric nanostructure of claim 3 wherein the functional group is selected from the group consisting of $SC_6H_{12}$, amine group ($-NH_2$) with 1 to 12 carbon spacers, thiol groups (SH) with 1 to 12 carbon spacers, biotin groups with 1 to 12 carbon spacers; triethylene glycol spacers, and acrylamide groups with 1 to 12 carbon spacers.

5. A geometric nanostructure of claim 1 wherein the nanoparticle-ligand complexes are affixed to each other through the hybridization of the distal portions of each single stranded DNA ligand.

6. A geometric nanostructure of claim 3 wherein the functional group is a first member of a binding pair and wherein the nanoparticle-ligand complexes are each affixed to a second member of a binding pair.

7. A geometric nanostructure of claim 6 wherein the first member of a binding pair is biotin and wherein the second member of a binding pair is selected from the group consisting of avidin and streptavidin.

* * * * *